United States Patent [19]
Spindel et al.

[11] Patent Number: 5,410,018
[45] Date of Patent: Apr. 25, 1995

[54] BOMBESIN-RELATED PEPTIDES

[75] Inventors: Eliot R. Spindel, Lake Oswegor; Srinivasa Nagalla; Brenda Barry, both of Portland, all of Oreg.

[73] Assignee: Oregon Regional Primate Research Center, Beaverton, Oreg.

[21] Appl. No.: 203,196

[22] Filed: Feb. 25, 1994

[51] Int. Cl.⁶ ............... A61K 37/00; A61K 31/445; A01N 43/40
[52] U.S. Cl. .................. 530/300; 514/14; 514/15; 530/327; 530/328
[58] Field of Search .............. 514/14, 15; 530/300, 530/327, 328

[56] References Cited

PUBLICATIONS

Gispamer et al. "Parallel biassays of 27 bombesin-like peptides"Regul. Pept. (1988) 21(1–2) p. 1–11.
Corjay, et al; "Two Distinct Bombesin Receptor Subtypes are Expressed and Functional in Human Lung Carcinoma Cells;" J. Biol. Chem. 266:18771 (1991).
Giladi, et al; "Simple Luminometric Assay to Detect Phosphoinositol-Linked Receptor Expression in Xenopus Oocytes;" BioTechniques 10:744 (1991).
Wei, et al. "Pituitary Adenylate Cyclase Activating Polypeptide-Induced Desensitization on Growth Hormone Release From Rat Primary Pituitary Cells;" Biochem. and Biophys. Research Comm. 197:1396–1401 (1993).
Nagalla, et al; "Gastrin-Releasing Peptide (GRP) is not Mammalian Bombesin;" J. Biol. Chem. 267:6916–6922 (1992).
Spindel, et al; "Cloning of cDNAs Encoding Amphibian Bombesin: Evidence for the Relationship Between Bombesin and Gastrin-Releasing Peptide;" Proc. Natl. Acad. Sci. USA 87:9813 (1990).
Spindel, et al; "Bombesin-Like Peptides: of Ligands and Receptors;" Recent Progress in Hormone Research 48:365 (1993).

*Primary Examiner*—Robert A. Wax
*Assistant Examiner*—Hyosuk Kim
*Attorney, Agent, or Firm*—Fish & Richardson

[57] ABSTRACT

A pure DNA encoding a peptide which encodes a novel bombesin-related peptide, i.e., H-pGlu-Gln-Ser-Leu-Gly-Asn-Gin-Trp-Ala-Arg-Gly-His-Phe-Met-NH$_2$ or Gly-Asn-Gln-Trp-Ala-Arg-Gly-His-Phe-Met-NH$_2$.
Also disclosed are a vector and a cell containing such a DNA, a pharmaceutical composition which includes such a peptide, and a method of preparing such a peptide by recombinant technology.

3 Claims, 4 Drawing Sheets

```
                                                         v10
           Met Ser Ala Ile Pro Leu Asn Arg Ile Leu Pro Leu Gly
TTAGAC ATG TCT GCG ATT CCT CTG AAC AGG ATC CTG CCT CTA GGG
                                  ^25 v20
Phe Leu Phe His Leu Leu Ile Phe Ser Phe Ile Ala Leu Ser
TTC CTA TTT CAC CTG CTG ATT TTC TCC TTC ATC GCT CTG TCC
       ^50                                  ^75 v30                                         v40
Ser Cys Met Glu Phe Val Glu Asp Pro Asn Asn Gln Gly Gly
AGC TGC ATG GAG TTC GTT GAA GAT CCC AAC AAT CAG GGC GGA
                 ^100                                ^125

═══        v50
Leu Ser Leu │Gln Gln Ser Leu Gly Asn Gln Trp Ala Arg Gly
CTC AGC CTG  CAG CAG TCG CTG GGG AAT CAG TGG GCA AGG GGT
                             ^150 v60
│His Phe Met Gly│Lys Lys Ser Leu Gln Asp Thr Asn Phe Gln
 CAC TTC ATG GGT AAG AAG AGC CTG CAG GAC ACA AAC TTT CAA
      ^175                                 ^200 v70                                     v80
Glu Met Glu Ser Phe Ala Lys Arg Asn Val Glu Asn Met Arg
GAG ATG GAA AGT TTT GCT AAA CGT AAT GTT GAG AAC ATG AGA
                 ^225                                ^250 v90
Ala Ala Leu Leu Gln Glu Gln Asn Arg Ala Glu Ser Glu Arg
GCT GCC CTC CTG CAG GAG CAG AAC AGA GCA GAA TCA GAA AGA
                          ^275 v100                                  v110
Glu Leu Arg Asn Val Gln Leu Ala Val Arg Asn Ile Leu Glu
GAG CTG CGG AAT GTA CAG TTG GCA GTA AGA AAC ATC TTG GAG
   ^300                                   ^325 v120
Gln Tyr Leu Lys Asn Met Gln Asn ter
CAG TAT CTG AAG AAT ATG CAG AAT TAG CAAA GAAATGTGTC
             ^350                              ^375

TTCCTGTACA (SEQ. ID NO: 5)     FIG. 1
```

BOMBESIN-RELATED PEPTIDES

Statement as to Federally Sponsored Research

This invention was made with support from the National Institute of Health (Grant No. R01-CA39237). Accordingly, the U.S. government has certain rights in the invention.

Field of the Invention

The present invention relates generally to the manipulation of genetic materials, and, more particularly, to recombinant DNA procedures which make possible the identification of DNA sequences encoding novel peptides.

Background of the Invention

Bombssin, a tetradecapeptide amide first isolated from the skin of the frog *Bombina bombina*, is a potent mitogen for mouse Swiss 3T3 fibroblast cells. It also stimulates secretion for guinea pig pancreatic acini. Bombssin-like peptides are produced and secreted by human small cell lung cancer cells and exogenously added bombssin-like peptides can stimulate the growth of human SCLC cells in vitro. Two examples of bombssin-like peptides are gastrin releasing peptide ("GRP") and Neuromedin B ("NMB").

GRP is a 27 amino acid peptide amide first isolated from the porcine gut. The C-terminal amino acid sequence of GRP is almost identical to that of bombssin. Neuromedin B is a decapeptide amide, the structure of which is almost identical to the last ten amino acids in the C-terminal region of GRP. Both GRP and Neuromedin B share amino acid sequence homology with bombssin and possess bombssin-like properties. Other bombesin-like peptides include litorin and Neuromedin C.

Recent structure-function and DNA cloning studies demonstrate that at least two classes of receptors mediate the action of bombesin-related peptides. One class, the GRP preferring subtype (GRP receptor), has a high affinity for GRP and a low affinity for NMB, whereas the other class, the NMB-preferring subtype (NMB receptor), has a high affinity for NMB and lower affinity for GRP. Both classes of receptors are widely present both in the central nervous system and in the gastrointestinal tract.

Summary of the Invention

The present invention features a pure DNA encoding a peptide which is a bombssin-related peptide and identified herein as SEQ ID NO: 1 (BIM-26337) or SEQ ID NO: 2 (BIM-26336). Preferably, the DNA of this invention consists essentially of a nucleotide sequence identified herein as SEQ ID NO: 3 or SEQ ID NO: 4.

Also within this invention is a vector or a cell containing one of the above-described DNA sequences. Preferably, in a cell which contains the DNA sequence of the invention, the DNA is introduced into the cell in a manner allowing the cell to express the peptide, e.g., by transforming or transfecting the cell with a vector containing the DNA sequence.

The present invention further features a pure peptide identified herein as SEQ ID NO: 1 or SEQ ID NO: 2.

It is a further feature of the present invention to prepare one of the above-described peptides by a DNA recombinant method which includes the steps of (i) introducing a DNA encoding the peptide into cells in a manner allowing the cells to express the peptide; (ii) culturing the cells in a medium; and (iii) recovering the expressed peptide.

What is meant by "pure DNA" herein is DNA that is not immediately contiguous with both of the coding sequences with which it is immediately contiguous (i.e., one at the 5' end and one at the 3' end) in the naturally-occurring genome of the organism from which the DNA of the invention is derived. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA or a genomic DNA fragment produced by the polymerase chain reaction technique or restriction endonuclease treatment) independent of other DNA sequences. It also includes a recombinant DNA which is part of a hybrid gene encoding additional polypeptide sequence.

A pure peptide, on the other hand, is a peptide free or substantially free of the components with which it is naturally associated.

The peptides of this invention can be provided in the form of pharmaceutically acceptable salts. Examples of preferred salts are those with therapeutically acceptable organic acids (e.g, acetic, lactic, maleic, citric, malic, ascorbic, succinic, benzoic, methanesulfonic, toluenesulfonic, or pamoic acid), as well as polymeric acids (e.g., tannic acid or carboxymethyl cellulose), and salts with inorganic acids as the hydrohalic acids (e.g., hydrochloric acid, sulfuric acid, or phosphoric acid).

In other preferred embodiments, a therapeutically effective amount of a peptide of this invention and a pharmaceutically acceptable carrier substance (e.g., magnesium carbonate, lactose, or a phospholipid with which the therapeutic compound can form a micelle) together form a therapeutic composition (e.g., a pill, tablet, capsule, or liquid) for administration (e.g., intravenously, subcutaneously, nasally, vaginally, or iontorphoretially) to a subject in need of the peptide. The pill, tablet, or capsule can be coated with a substance capable of protecting the composition from the gastric acid and intestinal enzymes in the subject's stomach for a period of time sufficient to allow the composition to pass undigested into the subject's small intestine. The therapeutic composition can also be in the form of a biodegradable or nonbiodegradable sustained release formulation for intramuscular administration (e.g., U.S. Pat. Nos. 4,675,189 and 4,767,628, hereby incorporated by reference). For maximum efficacy, zero order release is desired, and can be obtained using an implantable or external pump (e.g., INFUSAID TM pump) to administer the therapeutic composition.

Also within the scope of this invention are methods of using a peptide of this invention to treat diseases or disorders. Such utilities are well known to a person of ordinary skill in the art. For example, see U.S. Pat. No. 5,217,955, PCT WO 94/02018 and PCT WO 92/20363, all of which are hereby incorporated by reference.

The effective amount of the peptide of this invention to be used varies depending upon the manner of administration and the condition of the subject to be treated, and ultimately will be decided by the attending physician or veterinarian.

Other features and advantages of the invention will be apparent from the following description and from the claims.

Brief Description of the Drawings

The drawings are first briefly described.

Description of the Preferred Embodiments

Structure

We discovered that the peptides [Phe$^8$]phyllolitorin and [Leu$^8$] phyllolitorin are encoded in frogs of the sphilomedusa genus by two nearly identical DNA sequences which differ by only a single nucleotide. This finding suggested that highly similar DNA sequences might also encode multiple bombesin-like peptides in other species of frogs.

Skin, brain, and extracts of *Bombina orientalis*, a frog species that produces bombesin, were examined for the existence of multiple bombesin-like peptides by the following protocol:

Total RNA was prepared by homogenization of frog tissues in guanidine thiocyanate followed by centrifugation through CsCl. 5 μg total RNA was reverse transcribed with 25 pmole oligo(dT$^{18}$), 200 units of M-MLV reverse transcriptase (BRL), 5X Buffer (250 mM Tris-HCL, pH 8.3; 375 mM KCl, 15 nM MgCl$_2$, 50 mM DTT, 2.5 mM dNTP's) in 20 μl total volume at 37° C. for one hour. The entire reverse transcription was used in a 100 μl PCR reaction using 100 pmoles of a 5' primer ATTCCTCTGAACAGGATC and 100 pmoles of a 3' primer AAGTCCCATATCTCAGGC. These primers correspond, respectively, to positions 68–83 and 458–475 of the *Bombina orientalis* cDNA reported in Spindel, et al., Proc. Natl. Acad. Sci. USA 87:9813-17 (1990), which is hereby incorproated by reference.

PCR conditions were as follows: one cycle of 92° C.×1 min, 50° C.×2 min, 72° C.×5 min for a second strand synthesis followed by 35 cycles of 92° C.×2 min, 55° C.×1 min, 72° C.×2 min. 20 μl of the reaction was separated on a 1% agarose gel, blotted and hybridized to a $^{32}$P-end labeled internal oligonucleotide probe CATGGAGTTCGTTGAAGA. The hybridizing product was subcloned into PGEM-T vector (Promega) and sequenced according to standard procedures. See Negalla, et al., J. Biol. Chem. 267:6916–6922, which is hereby incorporated by reference.

Figure 1:
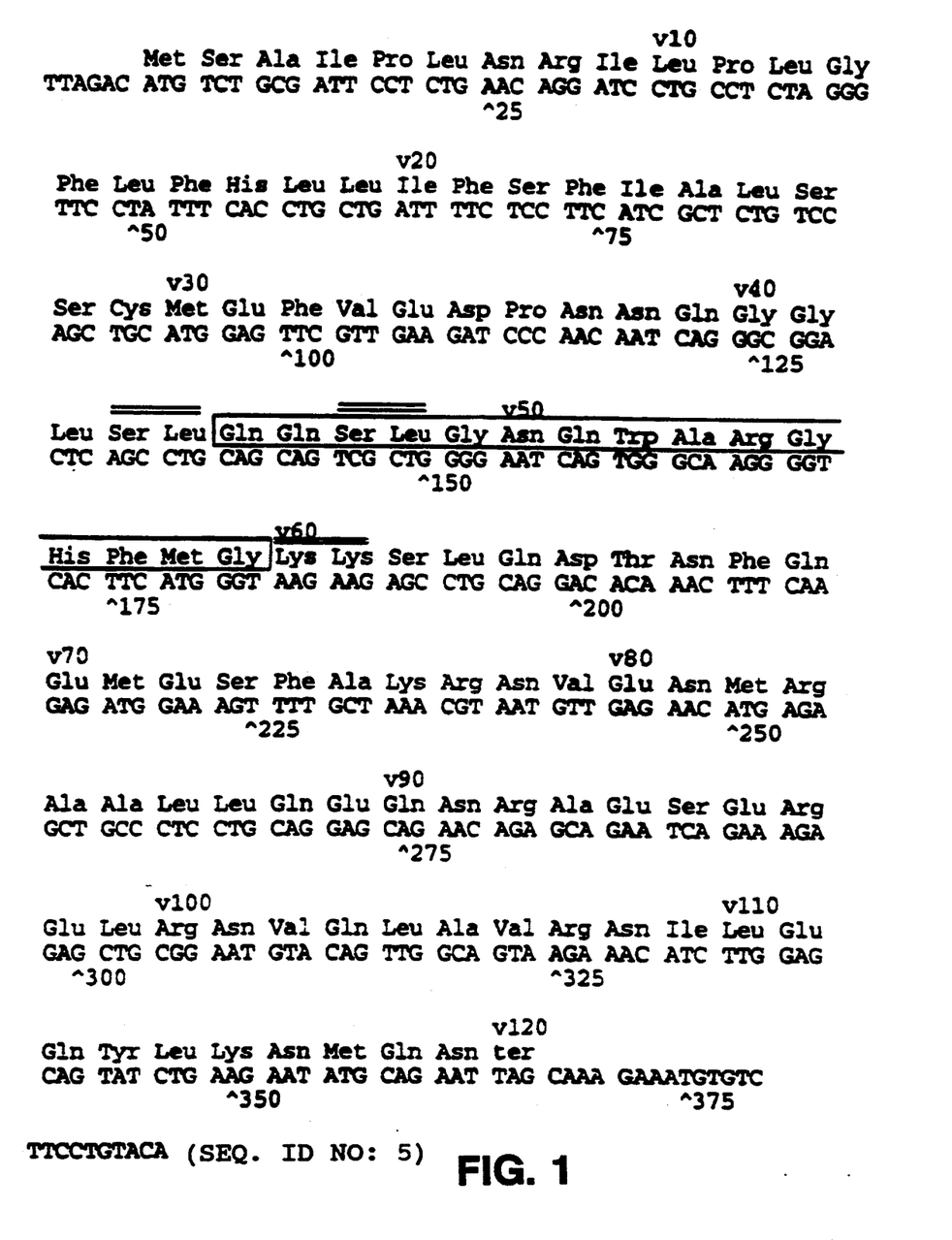
FIG. 1 is the sequence and translation of a cDNA encoding peptides of this invention, i.e., BIM-26336 and BIM-26337.

The nucleotide sequence of a frog cDNA thus obtained, as well as the deduced amino acid sequence, is shown in FIG. 1. A new bombesin-related peptide revealed by the deduced amino acid sequence, i e., [Ser$^3$, Arg$^{10}$, Phe$^{13}$] bombesin, is designated herein as "SAP bombesin." SAP bombesin-14 ("BIM-26337"): H-pGlu-Gln-Ser-Leu-Gly-Asn-Gln-Trp-Ala-Arg-Gly-His-Phe-Met-NH$_2$ ( SEQ ID NO: 1 )

All abbreviations of amino acids in this disclosure, with the exception of pGlu, stand for a residue with structure of —NH—CH(R)—CO—, wherein R is a side chain. The abbreviation pGlu stands for $$-\text{N}-\text{C}(\text{CH}_2)\frac{\text{O}}{2}-\text{CH}-\text{CO}-.$$

In FIG. 1, the sequence encoding SAP bombesin-14 and the glycine for the carboxy-terminal amide are boxed. The N-terminal Gln provides the amino-terminal pyroglutamyl residue of SAP bombesin-14. See Spindel et al., Proc. Natl. Acad. Sci. USA 87:9813 (1990). The C-terminal glycine serves as the amide donor for the C-terminal methionyl-amide reside of SAP bombesin-14. Bradbury et al., Nature 298:686 (1982). The three prohormone processing points, Ser-Leu, Ser-Leu and Lys-Lys, are double overlined. Douglas et al. Annu. Rev. Biochem., 53:665 (1984).

Because bombesin is cleaved from its precursor following the amino acids Ser-Leu, which are double overlined in FIG. 1, this dictates that SAP bombesin-14 is internally cleaved after the Ser-Leu to yield the following peptide:

SAP Bombesin-10 ("BIM-26336"): Gly-Asn-Gln-Trp-Ala-Arg-Gly-His-Phe-Met-NH$_2$ (SEQ ID NO: 2)

SAP bombesin-10 possesses homology to human NMB. That is, it differs from the human NMB by two amino acid residues: Gln vs. Leu at position 3 and Arg vso Thr at position 6.

SAP bombesin-14 and SAP bombesin-10 are encoded by the following segments in the cDNA sequence shown in FIG. 1, respectively:

| | |
|---|---|
| CAGCAGTCGCTGGGGAATCAGTGGGCAAGGGGTCACTTCATGGGT; | (SEQ ID NO: 3) |
| GGGAATCAGTGGGCAAGGGGTCACTTCATGGGT. | (SEQ ID NO: 4) |

Insertion of a bombesin-encoding sequence into an expression vector and introduction of the recombinant vector into a host cell are desirable. For example, an SAP bombesin can be produced by such a host cell. The techniques involved in recombinant production of peptides are well known to a person of ordinary skill in the art and in any event can be found in the literature, e.g., Sambrook, et al. Molecular Cloning, A Laboratory Manual, 2nd Ed. Cold Spring Harbor Laboratory Press, New York (1989), hereby incorporated by reference.

Function

I. Binding to Receptors

A. NMB Receptor

Membranes of the NMB receptor used in the binding assay were obtained by homogenizing rat olfactory bulb tissue (Polytron, setting 6, 15 sec) in ice-cold 50 mM Tris-HCl (Buffer A) and centrifuging twice as 39,000 x g (10 min), with an intermediate resuspension in fresh buffer. The final pellets were resuspended in the 50 mM Tris-HCl, containing 0.1 mg/ml bacitracin, and 0.1% BSA (Buffer B), and held on ice for the receptor binding assay. For the assay, aliquots (0.4 ml) were incubated with 0.05 ml [$^{125}$I] NMB (~2200 Ci/mmol, New England Nuclear) and Buffer B, with and without 0.05 ml of unlabeled competing peptides. The experiment was performed with BIM-26336, BIM-23337, GRP, and NMB as competing peptides.

After a 30 min incubation (4° C.), the bound [$^{125}$I]NMB was separated from the free by rapid filtration through GF/B filters which had been previously soaked in 0.3% polyethyleneimine. The filters were then washed three times with 5 ml aliquots of ice-cold Buffer A. Specific binding was defined as the total [125I] NMB bound minus that bound in the presence of 1 µM unlabeled NMB.

Figure 2:
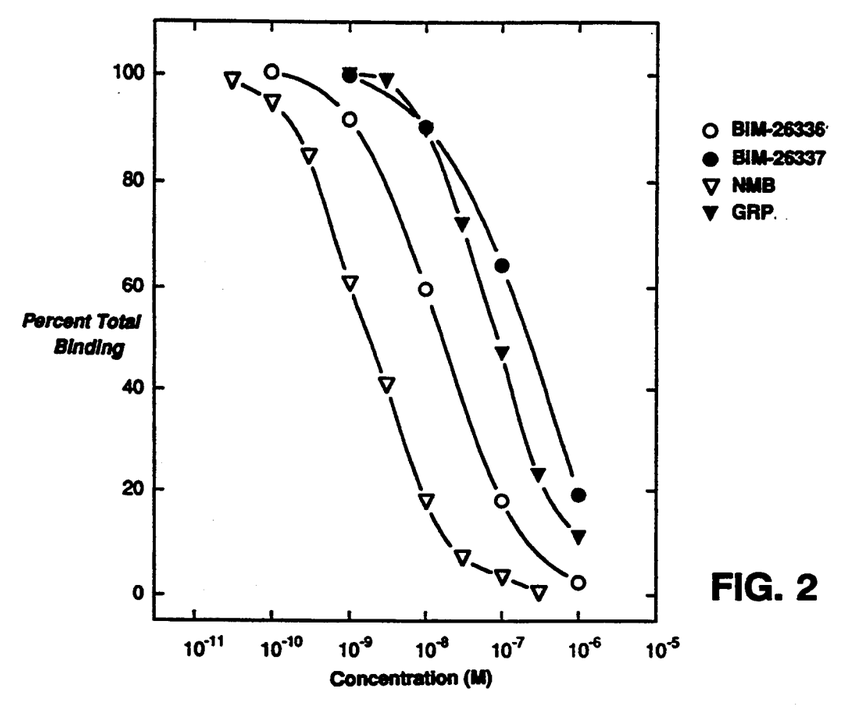
FIG. 2 is a graph showing the effect of BIM-26336 and BIM-26337 on the inhibition of [$^{125}$I] NMB binding.

The results of this experiment are presented on FIG. 2. BIM-26336 has a Ki value of 15.1 nM, while BIM26337 has a Ki value of 610 nM.

B. GRP Receptor

Membranes of the GRP receptor used in the binding assay were obtained by homogenizing cultured AR42J cells (Polytron, setting 6, 15 sec) in ice-cold 50 mM Tris-HCl (Buffer A) and centrifuging twice as 39,000 x g (10 min), with an intermediate resuspension in fresh buffer. The final pellets were resuspended in the 50 mM Tris-HCl, containing 0.1 mg/ml bacitracin, and 0.1% BSA (Buffer B), and held on ice for the receptor binding assay. For the assay, aliquots (0.4 ml) were incubated with 0.05 ml [$^{125}$I-Tyr$^4$] bombesin (~2200 Ci/mmol, New England Nuclear) and Buffer B, with and without 0.05 ml of unlabeled competing peptides. The experiment was performed with BIM-26336, BIM-23337, GRP, and NMB as competing peptides.

After a 30 min incubation (4° C.), the bound [$^{125}$I]-Tyr$^4$] bombesin was separated from the free by rapid filtration through GF/B filters which had been previously soaked in 0.3% polyethyleneimine. The filters were then washed three times with 5-ml aliquots of ice-cold Buffer A. Specific binding was defined as the total [$^{125}$I-Tyr$^4$] bombesin bound minus that bound in the presence of 1 µM unlabeled bombesin.

Figure 3:
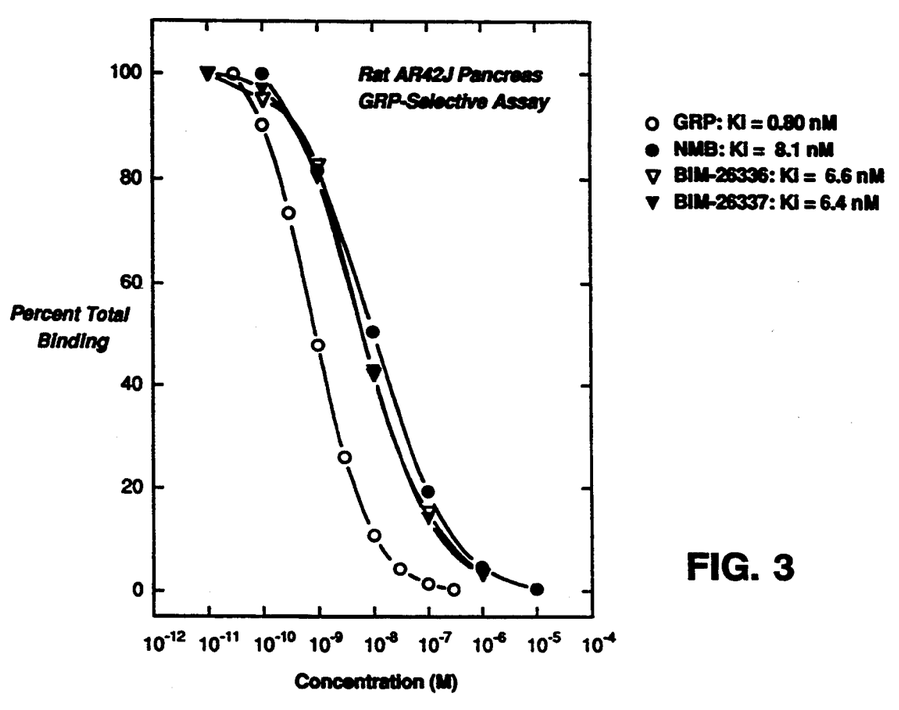
FIG. 3 is a graph showing the effect of BIM-26336 and BIM-26337 on the inhibition of [$^{125}$I-Tyr4] bombesin binding.

The results of this experiment are presented on FIG. 3. BIM-26336 has a Ki value of 6.6 nM, while BIM-26337 has a Ki value of 6.4 nM. BIM-26336, thus, effectively binds to both NMB and GRP receptors, while BIM-26337 possesses a more selective binding of GRP than NMB receptors.

II. Calcium Uptake Assay

The ability of BIM-26336 and BIM-26337 to activate both the GRP and NMB receptors were analyzed using a calcium uptake functional assay.

A. NMB Receptor

Xenopus oocytes, a frog egg naturally deprived of any receptors, were coinjected with both NMB receptor RNA and calcium photoprotein aequorin. The ability of SAP bombesins to induce change in intracellular calcium levels within the cells were measured luminometrically. See Spindel, et al., Recent Progress in Hormone Research 48:365 (1993); Corjay, et al., J. Biol. Chem. 266:18771 (1991); and Giladi et al., BioTechniques 10:744 (1991), all of which are hereby incorporated by reference.

Figure 4:
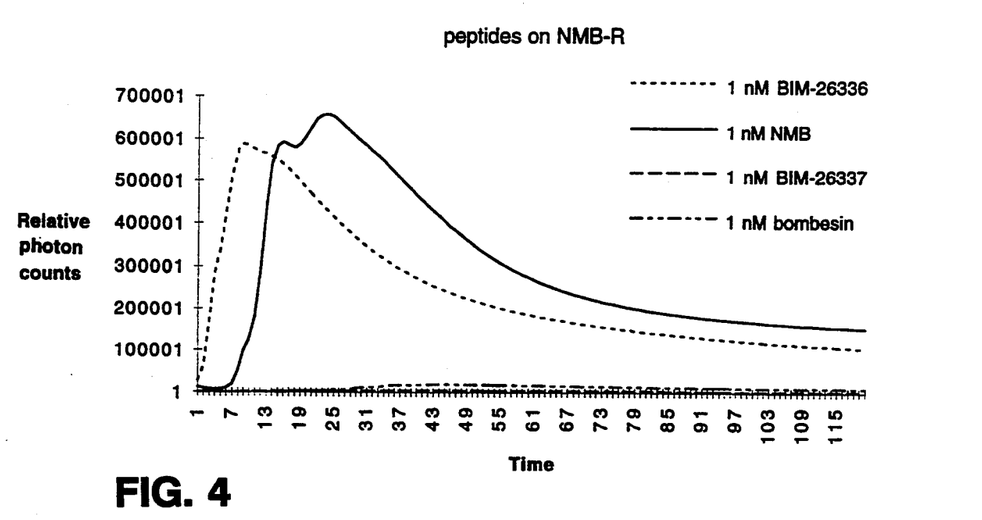
FIG. 4 is a graph showing the effect of BIM-26336 and BIM-26337 on calcium uptake in xenopus oocytes expressing the human NMB receptor.

The ability of bombesin, NMB, SAP bombesin-14, and SAP bombesin-10 to agonize the receptor was tested. FIG. 4 demonstrates the effect of these peptides on the level of intracellular calcium. The y-axis of the graph shows the relative luminometric response to the peptide while the xaxis depicts time elapsed in seconds. These results indicates that SAP bombesin-10 has nearly the same potency as NMB at the NMB receptor. The potency of SAP bombesin-14 and bombesin are approximately two log units less than that of NMB.

B. GRP Receptor

Xenopus oocytes were coinjected with both GRP receptor RNA and calcium photoprotein aequorin. The ability of SAP bombesins to induce change in intracellular calcium levels within the cells can be measured luminometrically.

Figure 5:
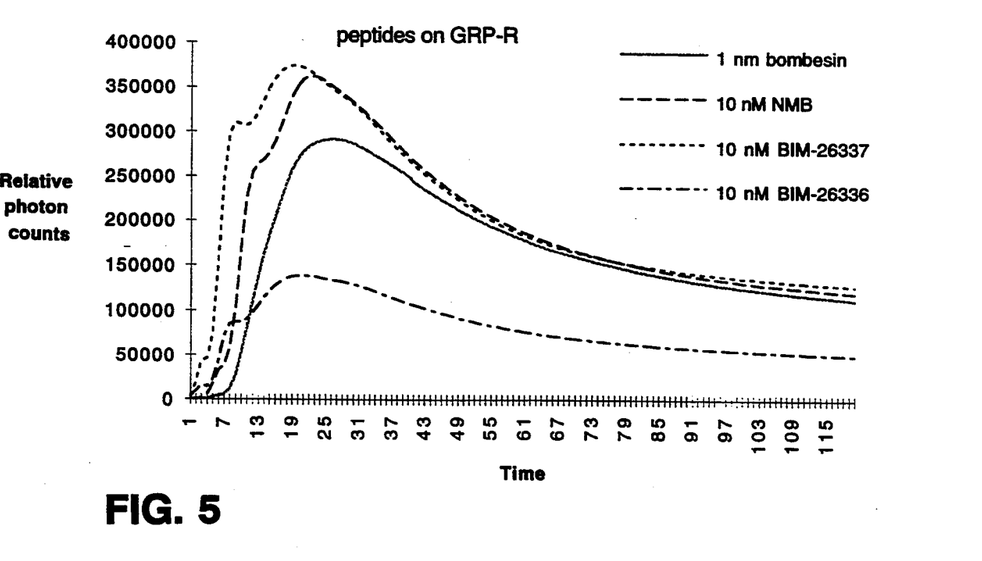
FIG. 5 is a graph showing the effect of BIM-26336 and BIM-26337 on calcium uptake in xenopus oocytes expressing the human GRP receptor.

The ability of bombesin, NMB, SAP bombesin-14, and SAP bombesin-10 to agonize the receptor was tested. FIG. 5 demonstrates the effect of these peptides on the level of intracellular calcium. The y-axis of the graph shows the relative luminometric response to the peptide while the x-axis depicts time elapsed in seconds. These results indicates that SAP bombesin-14 has a significantly greater potency than SAP bombesin-10 at the GRP receptor.

III. Thymidine Uptake Assay

Swiss 3T3/1R mouse embryo fibroblast cells were plated in 24 well tissue culture plates at a density of $2 \times 10^4$ cells in 1 ml of Dublbecco's modified eagles medium (DMEM) supplemented with 40 mM glutamine (Gln) in 10% fetal bovine serum. Cells were incubated 3 or 4 days at 37% in a humidified atmosphere at 95% air/5% $CO_2$ before replacing the growth medium with DMEM/Gln and 250 µg/ml gentamicin. On the following day, 1 µCi thymidine was added to all wells, and activity was addressed by addition of test peptides alone or in the presence on 3 nM bombesin, respectively. After 24 h, the cells were rinsed with icecold isotonic saline and treated with ice-cold 5% trichloroacetic acid for 30 min. Cells were then rinsed with 95% ethanol and incubated with 0.1 N NaOH overnight at room temperature. One ml aliquots of neutralized samples were counted in a Packard Tri-Carb liquid scintillation analyzer. Test sample activity was measured in 2 independent experiments performed in quadruplicate.

Figure 6:
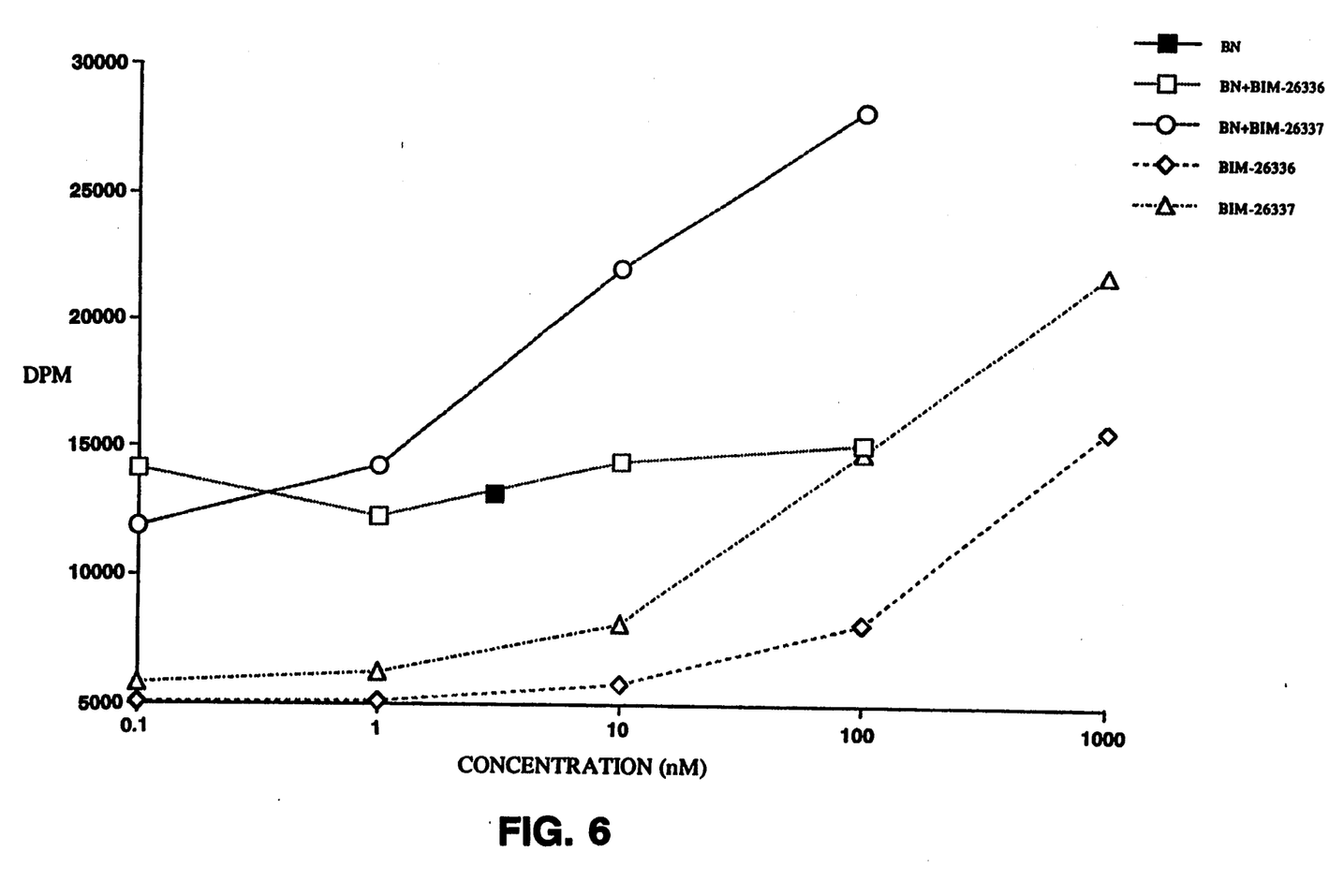
FIG. 6 is a graph showing the effect of BIM-26336 and BIM-26337 on thymidine uptake in 3T3 cells ("BN" stands for bombesin).

This experiment was performed using 5 test samples: (1) bombesin (3 nM); (2) BIM-26336; (3) BIM-26337; (4) bombesin (3 nM) and BIM-26336; and (5) bombesin (3 nM)+BIM-26337. The results of these experiments are depicted on FIG. 6, wherein the x-axis depicts concentration of the respective SAP bombesin and the y-axis depicts disintegration per minute. The graph thus shows that both BIM-26336 and BIM-26337 induce thymidine uptake. Surprisingly, this effect is also substantially enhanced with the addition of a slight concentration of bombesin (3 nM).

Other Embodiments

The invention includes any peptide which is substantially homologous (i.e., 80% or greater) to SAP bombesins identified above as SEQ ID NO: 1 and SEQ ID NO: 2. "Homologous" refers to the sequence similarity between two peptides. When a position in both of the two compared sequences is occupied by identical amino acid monomeric subunits, it is homologous at that position. The homology between two sequences is a function of the number of matching or homologous positions shared by the two sequences. For example, if 8 of 10 of the positions in two sequences are occupied by identical amino acids then the two sequences are 80% homologous.

Other SAP bombesins which are also included in this invention are allelic variations, mammalian analogs, natural mutants, induced mutants, peptides encoded by DNA that hybridizes under high or low stringency conditions (see below) to SEQ ID NO: 3 or SEQ ID NO: 4, and peptides specifically bound by antisera to SEQ ID NO: 1 or SEQ ID NO: 2.

The invention also includes a pure DNA characterized as including a sequence which hybridizes under highly stringent conditions (e.g., as described in Sambrook et al., Molecular Cloning: A Laboratory Manual, Cold Spring Harbor Laboratory, Cold Spring Harbor, N.Y., 1989, hereby incorporated by reference) to a nucleic acid probe which includes at least a six-nucleotide segment (preferably at least 10 nucleotides) of SEQ ID NO: 3 or SEQ ID NO: 4. Alternatively, the DNA of the invention may be characterized as being capable of hybridizing under low-stringency conditions to a nucleic acid probe which includes the coding sequence of SEQ ID NO: 3 or SEQ ID NO: 4. An example of such low-stringency conditions is as follows: prehybridization in 50% formamide, 5X SSC, 25 mM potassium phosphate buffer (pH 7.4), 5X Denhardt's, and 50 μg/ml denatured salmon sperm DNA for 4–12 hours at 20° C.; hybridization for 12–24 hours at 20° C.; and washing in 5X SSC containing 0.1% SDS, at 20° C.

The invention also includes any biologically active analog of SEQ ID NO: 1 or SEQ ID NO: 2. By "biologically active" is meant possessing at least 75% of the activity of bombesin or neuromedin.

Analogs can differ from naturally occurring SAP bombesins in amino acid sequence or can be modified in ways that do not involve the sequence, or both. Alterations in primary sequence include genetic variants, both natural and induced. Also included are analogs that include residues other than naturally occurring L-amino acids.

Other embodiments are also within the following claims.

What is claimed is:

1. A pure peptide selected from the group consisting of SEQ ID NO: 1 and SEQ ID NO: 2.

2. The peptide of claim 1, wherein said peptide is SEQ ID NO: 1.

3. The peptide of claim 13, wherein said peptide is SEQ ID NO: 2.

* * * * *

UNITED STATES PATENT AND TRADEMARK OFFICE
CERTIFICATE OF CORRECTION

PATENT NO. : 5,410,018
DATED : April 25, 1995
INVENTOR(S) : Eliot R. Spindel, Srinivasa Nagalla, and Brenda Barry It is certified that error appears in the above-indentified patent and that said Letters Patent is hereby corrected as shown below:

On the title page:

In the Abstract, line 3, replace "Gly-Asn-Gin-Trp..." with --Gly-Asn-Gln-Trp... --;

Col. 1, line 17, replace "Bombssin" with --Bombesin--;

Col. 1, line 22, replace "Bombssin-like peptides" with --Bombesin-like peptides--;

Col. 1, line 24, replace "bombssin-like peptides" with --bombesin-like peptides--;

Col. 1, line 25, replace "bombssin-like peptides" with --bombesin-like peptides--;

UNITED STATES PATENT AND TRADEMARK OFFICE
CERTIFICATE OF CORRECTION

PATENT NO. : 5,410,018
DATED : April 25, 1995
INVENTOR(S) : Eliot R. Spindel, Srinivasa Nagalla, and Brenda Barry It is certified that error appears in the above-indentified patent and that said Letters Patent is hereby corrected as shown below:

Col. 1, line 30, replace "bombssin" with --bombesin--;

Col. 1, line 35, replace "bombssin and possess bombssin-like properties" with --bombesin and possess bombesin-like properties--;

Col. 1, line 51, replace "bombssin-related peptide" with --bombesin-related peptide--;

Col. 5, line 63, replace "xaxis" with --x-axis--;

Col. 6, line 27, replace "icecold" with --ice-cold--.

Signed and Sealed this

Twenty-seventh Day of June, 1995

BRUCE LEHMAN

Attest:

Attesting Officer

Commissioner of Patents and Trademarks

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
       ( A ) LENGTH: 14
       ( B ) TYPE: amino acid
       ( C ) STRANDEDNESS:
       ( D ) TOPOLOGY: linear ( i x ) FEATURE:
       ( D ) OTHER INFORMATION: Xaa is pGlu ( x i ) SEQUENCE DESCRIPTION: SEQ ID NO: 1:

Xaa  Gln  Ser  Leu  Gly  Asn  Gln  Trp  Ala  Arg  Gly  His  Phe  Met
                     5                              10

( 2 ) INFORMATION FOR SEQ ID NO: 2:

( i ) SEQUENCE CHARACTERISTICS:
       ( A ) LENGTH: 10
       ( B ) TYPE: amino acid
       ( C ) STRANDEDNESS:
       ( D ) TOPOLOGY: linear ( x i ) SEQUENCE DESCRIPTION: SEQ ID NO: 2:

Gly  Asn  Gln  Trp  Ala  Arg  Gly  His  Phe  Met
                5                              10

( 2 ) INFORMATION FOR SEQ ID NO: 3:

( i ) SEQUENCE CHARACTERISTICS:
       ( A ) LENGTH: 45
       ( B ) TYPE: nucleic acid
       ( C ) STRANDEDNESS: single
       ( D ) TOPOLOGY: linear ( x i ) SEQUENCE DESCRIPTION: SEQ ID NO: 3:

CAGCAGTCGC  TGGGGAATCA  GTGGGCAAGG  GGTCACTTCA  TGGGT                    4 5

( 2 ) INFORMATION FOR SEQ ID NO: 4:

( i ) SEQUENCE CHARACTERISTICS:
       ( A ) LENGTH: 33
       ( B ) TYPE: nucleic acid
       ( C ) STRANDEDNESS: single
       ( D ) TOPOLOGY: linear ( x i ) SEQUENCE DESCRIPTION: SEQ ID NO: 4:

GGGAATCAGT GGGCAAGGGG TCACTTCATG GGT                                          33

( 2 ) INFORMATION FOR SEQ ID NO: 5:

( i ) SEQUENCE CHARACTERISTICS:
        ( A ) LENGTH: 390
        ( B ) TYPE: nucleic acid
        ( C ) STRANDEDNESS: single
        ( D ) TOPOLOGY: linear     ( x i ) SEQUENCE DESCRIPTION: SEQ ID NO: 5:

```
TTAGAC ATG TCT GCG ATT CCT CTG AAC AGG ATC CTG CCT CTA GGG TTC            48
       Met Ser Ala Ile Pro Leu Asn Arg Ile Leu Pro Leu Gly Phe
        1           5                  10

CTA TTT CAC CTG CTG ATT TTC TCC TTC ATC GCT CTG TCC AGC TGC ATG           96
Leu Phe His Leu Leu Ile Phe Ser Phe Ile Ala Leu Ser Ser Cys Met
15              20                  25                  30

GAG TTC GTT GAA GAT CCC AAC AAT CAG GGC GGA CTC AGC CTG CAG CAG          144
Glu Phe Val Glu Asp Pro Asn Asn Gln Gly Gly Leu Ser Leu Gln Gln
            35                  40                  45

TGC CTG GGG AAT CAG TGG GCA AGG GGT CAC TTC ATG GGT AAG AAG AGC          192
Cys Leu Gly Asn Gln Trp Ala Arg Gly His Phe Met Gly Lys Lys Ser
        50                  55                  60

CTG CAG GAC ACA AAC TTT CAA GAG ATG GAA AGT TTT GCT AAA CGT AAT          240
Leu Gln Asp Thr Asn Phe Gln Glu Met Glu Ser Phe Ala Lys Arg Asn
65                  70                  75

GTT GAG AAC ATG AGA GCT GCC CTC CTG CAG GAG CAG AAC AGA GCA GAA          288
Val Glu Asn Met Arg Ala Ala Leu Leu Gln Glu Gln Asn Arg Ala Glu
80                  85                  90                  95

TCA GAA AGA GAG CTG CGG AAT GTA CAG TTG GCA GTA AGA AAC ATC TTG          336
Ser Glu Arg Glu Leu Arg Asn Val Gln Leu Ala Val Arg Asn Ile Leu
            100                 105                 110

GAG CAG TAT CTG AAG AAT ATG CAG AAT TAG CAAAGAAATG TGTCTTCCTG            386
Glu Gln Tyr Leu Lys Asn Met Gln Asn
            115                 120

TACA                                                                     390
```